(12) United States Patent
Fulkerson et al.

(10) Patent No.: US 10,613,048 B2
(45) Date of Patent: Apr. 7, 2020

(54) METHOD AND SYSTEM OF MONITORING ELECTROLYTE LEVELS AND COMPOSITION USING CAPACITANCE OR INDUCTION

(71) Applicant: Fresenius Medical Care Holdings, Inc., Waltham, MA (US)

(72) Inventors: Barry Neil Fulkerson, Longmont, CO (US); Gregory Hayes Gengarelly, Laguna Hills, CA (US); Tam Nolan, Oceanside, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 51 days.

(21) Appl. No.: 15/988,214

(22) Filed: May 24, 2018

(65) Prior Publication Data

US 2018/0348156 A1 Dec. 6, 2018

Related U.S. Application Data

(63) Continuation of application No. 14/924,134, filed on Oct. 27, 2015, now Pat. No. 10,006,878, which is a continuation of application No. 13/725,178, filed on Dec. 21, 2012, now Pat. No. 9,201,036.

(51) Int. Cl.
| | |
|---|---|
| *G01N 27/22* | (2006.01) |
| *A61M 1/14* | (2006.01) |
| *A61M 1/16* | (2006.01) |
| *G01F 23/26* | (2006.01) |

(52) U.S. Cl.
CPC .............. *G01N 27/22* (2013.01); *A61M 1/14* (2013.01); *A61M 1/1603* (2014.02); *A61M 1/1605* (2014.02); *A61M 1/1668* (2014.02); *G01F 23/268* (2013.01); *G01N 27/226* (2013.01); *G01N 27/228* (2013.01); *A61M 2205/123* (2013.01); *A61M 2205/3317* (2013.01); *A61M 2205/3368* (2013.01); *A61M 2205/3389* (2013.01)

(58) Field of Classification Search
CPC .... G01N 27/22; G01N 27/226; G01N 27/228; G01F 23/268; A61M 1/14; A61M 1/1603; A61M 1/1605; A61M 1/1668; A61M 2205/123; A61M 2205/3368; A61M 2205/3389; A61M 2205/3317
See application file for complete search history.

(56) References Cited

U.S. PATENT DOCUMENTS

| | | | | |
|---|---|---|---|---|
| 3,375,716 | A * | 4/1968 | Hersch | G01F 23/266 |
| | | | | 73/304 C |
| 5,135,485 | A * | 8/1992 | Cohen | A61M 5/1684 |
| | | | | 324/606 |
| 6,943,566 | B2 * | 9/2005 | Florin | G01F 23/266 |
| | | | | 324/662 |

* cited by examiner

*Primary Examiner* — John Kim
(74) *Attorney, Agent, or Firm* — Novel IP

(57) ABSTRACT

Methods and systems for monitoring fluid levels and electrolyte levels used in a dialysis machine. A receptacle, configured to receive a container, comprises a plurality of curved side panels and a base to form a cylindrical shaped cavity for receiving a container. Each panel includes a conductive material on its inner surface and, optionally, a shielding on its outer surface. An electronics component housed within, or near, the receptacle drives the capacitive process and interprets generated data to determine fluid levels and compositions. An alternate receptacle includes one or two coils wrapped about the container and uses induction to determine fluid level.

21 Claims, 5 Drawing Sheets

METHOD AND SYSTEM OF MONITORING ELECTROLYTE LEVELS AND COMPOSITION USING CAPACITANCE OR INDUCTION

CROSS-REFERENCE

The present application is a continuation application of U.S. patent application Ser. No. 14/924,134, entitled "Method and System of Monitoring Electrolyte Levels and Composition Using Capacitance or Induction" and filed on Oct. 27, 2015, now U.S. Pat. No. 10,006,878, which is a continuation application of U.S. patent application Ser. No. 13/725,178, of the same title, filed on Dec. 21, 2012, and issued as U.S. Pat. No. 9,201,036 on Dec. 1, 2015.

FIELD

The present specification relates generally to fluid monitoring in dialysis systems. More particularly, the present specification relates to methods and systems using capacitance to monitor dialysis electrolyte fluid levels and composition.

BACKGROUND

Blood purification systems, which are used for conducting hemodialysis, hemodiafiltration or hemofiltration, involve the extracorporeal circulation of blood through an exchanger having a semi permeable membrane. Such systems further include a hydraulic system for circulating blood and a hydraulic system for circulating replacement fluid or dialysate comprising the certain blood electrolytes in concentrations close to those of the blood of a healthy subject. Standard dialysis treatment comprises two phases, namely, (a) dialysis, in which toxic substances and scoriae (normally small molecules) pass through the semi-permeable membrane from the blood to the dialysis liquid, and (b) ultrafiltration, in which a pressure difference between the blood circuit and the dialysate circuit, more precisely a reduced pressure in the latter circuit, causes the blood content of water to be reduced by a predetermined amount.

During dialysis treatment, the dialysate is stored locally for infusion into the treatment process as needed. A standard cylindrical container is filled with various compositions and non-sterile or sterile water to produce the electrolyte or infusate. A tube is placed within the mixture for drawing the electrolyte into the filtering components of the dialysis machine. In order to properly perform the dialysis procedure, the amount and composition of the electrolyte must be continuously and accurately monitored.

One method of monitoring involves using an optical camera and a weight scale to monitor the composition and amount, respectively, of the electrolyte. For example, U.S. patent application Ser. No. 13/023,490, entitled "Portable Dialysis Machine", filed on Feb. 8, 2011 and assigned to the applicant of the present invention, describes how "desired quantities of an infusate solution can be added to the dialysis fluid. Infusate is a solution containing minerals and/or glucose that help replenish minerals like potassium and calcium in the dialysate fluid at levels after undesired removal by the sorbent. A peristaltic pump is provided to pump the desired amount of infusate solution to [a] container. A camera may optionally be provided to monitor the changing liquid level of the infusate solution as a safety check warning of infusate flow failure . . . . The container is also equipped with a scale for keeping track of the weight, and therefore volume, of the fluid in the container." U.S. patent application Ser. No. 13/023,490 is incorporated herein by reference in its entirety.

Although the use of a camera and scale provides a mechanism for monitoring the level and composition of electrolyte, an improved, non-invasive system to monitor electrolytes, while requiring fewer components and being more inexpensive and easier to commercially implement, is still needed.

SUMMARY

The present specification is directed toward a system for monitoring electrolyte of a dialysis machine, comprising: a cylindrical shaped receptacle configured to receive a container, wherein said receptacle comprises an even numbered plurality of curved panels arranged in a substantially circular or semi-circular pattern atop a base, wherein each of said panels comprises a concave inner surface facing said container and an outer surface opposite said inner surface and wherein each of said panels includes a conductive material on its inner surface and a shielding material on its outer surface. Each panel is electrically isolated from each other panel. A container houses the electrolytes and is configured to fit within the receptacle. Electronics are housed within the receptacle and are adapted to drive a capacitive process to generate characteristic data of the electrolytes. The electronics interpret the data to provide a user with information regarding the fluid level and composition of the electrolytes.

In one embodiment, the electronics are housed in the base of the receptacle. In another embodiment, the electronics are housed in a compartment positioned on an external side of the receptacle.

In one embodiment, the conductive material is copper. In one embodiment, the shielding material is also copper.

In one embodiment, each panel further comprises two side surfaces normal to the outer surface, wherein each side surface includes a fin extending outwardly from and extending along the entire vertical length of each side surface such that two opposing fins are in physical contact at said base of said receptacle but do not touch at the top edge of the receptacle.

The present specification is also directed toward a method of monitoring electrolytes used in a dialysis machine by providing a receptacle system adapted to inductively measure electrolytes. The receptacle system includes a substantially cylindrically shaped receptacle configured to receive a container, wherein said receptacle comprises a plurality of curved panels arranged in a circular pattern atop a base. Each of the panels comprises a curved inner surface facing the container and an outer surface opposite the inner surface. Each of the panels also includes a metallic material on its inner surface and a shielding material on its outer surface. Preferably, each panel is electrically isolated from the other panels. In one embodiment, the receptacle houses the electronics and is configured to receive an electrolyte container where the electrolyte container is operatively connected to a fluid circuit of the dialysis machine. The method further includes 1) performing a dialysis treatment on a patient using the machine and operating the electronics to generate an alternating current (AC) excitation of the conductive material on the inner surface of the at least one panel, 2) measuring the coupled response in the conductive material on the inner surface of the opposing panel to determine capacitance, and 3) comparing the measured capacitance with the predetermined capacitance of known liquids to determine the fluid level and composition of the electrolyte.

The present specification is also directed toward a system for monitoring electrolytes in a fluid used in a dialysis procedure, comprising: a cylindrical shaped receptacle configured to receive a container for holding the electrolytes, wherein said receptacle comprises a base from which extends a pair of intertwined, mutually shielded conductive coils that wrap around said container and electronics housed within the receptacle, wherein, said electronics drive a mutual inductive process to generate characteristic data of the electrolytes and wherein said electronics interpret said data to provide a user with information regarding the fluid level of the electrolytes.

In one embodiment, the system for monitoring the electrolytes of a dialysis machine further comprises at least one temperature sensor to measure the temperature of said electrolytes.

In one embodiment, the electronics are housed in the base of the receptacle. In another embodiment, the electronics are housed in a compartment positioned on an external side of the receptacle.

In one embodiment, the conductive coils are made of copper.

The present specification also discloses a method of monitoring electrolytes in a fluid for use in a dialysis machine by providing an electrolyte container and receptacle system. The receptacle system comprises a receptacle configured to receive a container, wherein said receptacle comprises a base from which extends a pair of intertwined, mutually shielded conductive coils that wrap around the container, electronics, and a container for holding the electrolytes in fluid and configured to fit within the receptacle. The method operatively connects said electrolyte container and receptacle system to the dialysate circuit of a dialysis machine, performs a dialysis treatment on a patient using the dialysis machine, operates the electronics to generate an alternating current (AC) excitation of one of said pair of conductive coils, and measures the coupled response in the other coil on the opposing side of the container to determine mutual inductance. The measured inductance is then compared with the predetermined inductance of known liquids to determine the fluid level of the electrolytes.

In one embodiment, the electrolyte container and receptacle system further includes at least one temperature sensor. The method of monitoring electrolytes further comprises the steps of: measuring the temperature of the electrolytes using said at least one temperature sensor, applying a function to said temperature measurement and said measured inductance to yield an output, and comparing said output to comparable data for compositions of known liquids to determine the composition of said electrolyte.

The present specification is also directed toward a system for monitoring electrolytes of a dialysis machine, comprising: a cylindrically shaped receptacle configured to receive a container, wherein said receptacle comprises a base from which extends a single shielded conductive coil that wraps around said container, electronics housed within the receptacle, and a container for holding electrolytes and configured to fit within said receptacles, where the electronics drive a single inductive process to generate characteristic data of the electrolytes and wherein the electronics interpret the data to provide a user with information regarding the fluid level of the electrolytes.

In one embodiment, the system for monitoring the electrolytes used in a dialysis machine further comprises at least one temperature sensor to measure the temperature of said electrolytes.

In one embodiment, the electronics are housed in said base of said receptacle. In another embodiment, the electronics are housed in a compartment positioned on an external side of the receptacle.

In one embodiment, the conductive coil is composed of copper.

The present specification is also directed toward a method of monitoring electrolytes in a fluid used in one or more fluid circuits of a dialysis machine. The method comprising the steps of: placing a container in a receptacle, wherein said receptacle comprises a base from which extends a single shielded conductive coil that wraps around the container and wherein the receptacle houses electronics, operatively connecting said electrolyte container and receptacle system to the dialysate circuit of a dialysis machine, performing dialysis treatment on a patient using said machine, operating said electronics to generate an alternating current (AC) excitation of said single conductive coil, measuring the coupled response in the coil on the opposing side of the container to determine single inductance, and comparing the measured inductance with the predetermined inductance of known liquids to determine the fluid level of the electrolyte.

In one embodiment, the electrolyte container and receptacle system further includes at least one temperature sensor. The method of monitoring the electrolytes further comprises the steps of: measuring the temperature of said electrolytes using said at least one temperature sensor, combining said temperature measurement with said measured inductance, and comparing said combined data to temperature and inductance data for compositions of known liquids to determine the composition of said electrolyte.

The present specification is also directed toward a system for monitoring electrolytes in a fluid used in a dialysis machine, comprising: a receptacle configured to receive a container, wherein said receptacle comprises an even numbered plurality of panels arranged in a pattern atop a base, wherein each of said panels comprises a concave inner surface facing said container and an outer surface opposite said inner surface, wherein each of said panels has a conductive material on its inner surface, and wherein each panel is electrically isolated from each other panel; and a circuit in electrical communication with at least one of said plurality of panels; wherein said circuit is configured to drive a capacitive process to generate characteristic data of said electrolytes.

In one embodiment, the receptacle in combination with said plurality of panels forms a structure defining a cavity that is substantially cylindrical.

In one embodiment, the circuit is housed within the base of the receptacle. In another embodiment, the circuit is housed in a compartment located external to said receptacle.

In one embodiment, the conductive material is copper. In one embodiment, the outer surface comprises a shielding material wherein the shielding material is copper.

In one embodiment, each panel further comprises two side surfaces normal to said outer surface wherein each side surface includes a fin extending outwardly from, and along, the entire vertical length of each side surface. In one embodiment, the receptacle comprises four panels wherein the fins of adjacent panels are in physical contact at said base of said receptacle but do not touch at the top edge of said receptacle.

In one embodiment, the system for monitoring electrolytes further comprises a container for holding electrolytes and configured to snugly fit within said receptacle.

In one embodiment, the circuit drives the capacitive process to generate characteristic data of said electrolytes by generating an alternating current in a form of a stimulation wave and transmitting such wave to at least one of said plurality of panels and receiving a responsive wave generated by a panel opposing said one of said plurality of panels. In one embodiment, the circuit drives the capacitive process to generate characteristic data of said electrolytes by further comparing data derived from said responsive wave to predetermined capacitance data for liquids with known levels and electrolyte compositions and determining a fluid level and a composition of the electrolytes in said fluid based on the data derived from the responsive wave and predetermined capacitance data.

In one embodiment, the receptacle further comprises a temperature sensor wherein the circuit is configured to receive data indicative of a temperature from the temperature sensor, apply a function of said data and data generated from said capacitive process to generate an output, and compare said output to data derived from compositions of liquids having known levels of electrolytes and temperatures, and, based on said comparison, determine a composition of said electrolytes in said fluid.

The present specification is also directed toward a method of monitoring a fluid having a fluid level and electrolytes in a dialysis system, said method comprising the steps of: providing a receptacle configured to receive a container, wherein said receptacle comprises a base, a first panel attached to said base, a second panel attached to said base, and circuitry in electrical communication with said first panel and said second panel, wherein each of said first and second panels comprises a curved inner surface facing said container, wherein each of said first and second panels includes a conductive material on its inner surface, and wherein each panel is electrically isolated from each other panel; filling the container with water and electrolytes; operatively connecting a fluid flow path from a dialysate circuit in the dialysis system to said container; performing a dialysis treatment on a patient using said dialysate circuit; and, operating said circuit to generate an electrical excitation of the conductive material on the inner surface of the first panel; measuring a capacitance arising from the electrical excitation of the conductive material on the inner surface of the first panel in the second panel; determine the fluid level and composition of the electrolytes based on said measured capacitance.

In one embodiment, the electrolytes are at least one of potassium, magnesium, or calcium.

In one embodiment, the circuitry comprises a processor and memory storing programmatic instructions that, when executed, generates an alternating current in a form of a stimulation wave and transmits such wave to the first panel.

In one embodiment, the circuitry comprises a processor and memory storing programmatic instructions that, when executed, receives and processes a responsive signal generated by the second panel in response to an electrical stimulation of the first panel.

In one embodiment, the circuitry comprises a processor and memory storing programmatic instructions that, when executed, compares data derived from said responsive signal to predetermined capacitance data for liquids with known levels and known electrolyte compositions.

In one embodiment, the circuitry comprises a processor and memory storing programmatic instructions that, when executed, determines a fluid level and a composition of the electrolytes in said fluid based on the data derived from the responsive signal and said predetermined capacitance data.

In one embodiment, the circuitry comprises a processor and memory storing programmatic instructions that, when executed, receives data indicative of a temperature from a temperature sensor, applies a function of said data indicative of a temperature and data derived from the responsive signal to generate an output, compares said output to data derived from compositions of liquids having known levels of electrolytes and temperatures, and, based on said comparison, determines a composition of said electrolytes in said fluid.

The present specification is also directed toward a dialysis system that monitors a level of a fluid and a composition of electrolytes in said fluid, comprising: a dialysis machine for performing a dialysis treatment on a patient; a receptacle configured to receive a cylindrical container, wherein said receptacle comprises a base from which extends a pair of intertwined, mutually shielded conductive coils that substantially encircle said container; and a circuit housed within the base of the receptacle, wherein the circuit drives an inductive process to generate data indicative of a composition of said electrolytes in the fluid, generates data indicating the level of the fluid, and transmits said data indicative of the composition of said electrolytes and data indicating the level of the fluid level to the dialysis machine.

The present specification is also directed toward a dialysis system that monitors a level of a fluid and a composition of electrolytes in said fluid, comprising: a dialysis machine for performing a dialysis treatment on a patient; a receptacle configured to receive a cylindrical container, wherein said receptacle comprises a base from which extends a single shielded conductive coil that substantially encircles said container; and a circuit housed within the base of the receptacle, wherein the circuit drives an inductive process to generate data indicative of a composition of said electrolytes in the fluid, generates data indicating the level of the fluid, and transmits said data indicative of the composition of said electrolytes and data indicating the level of the fluid level to the dialysis machine.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1:
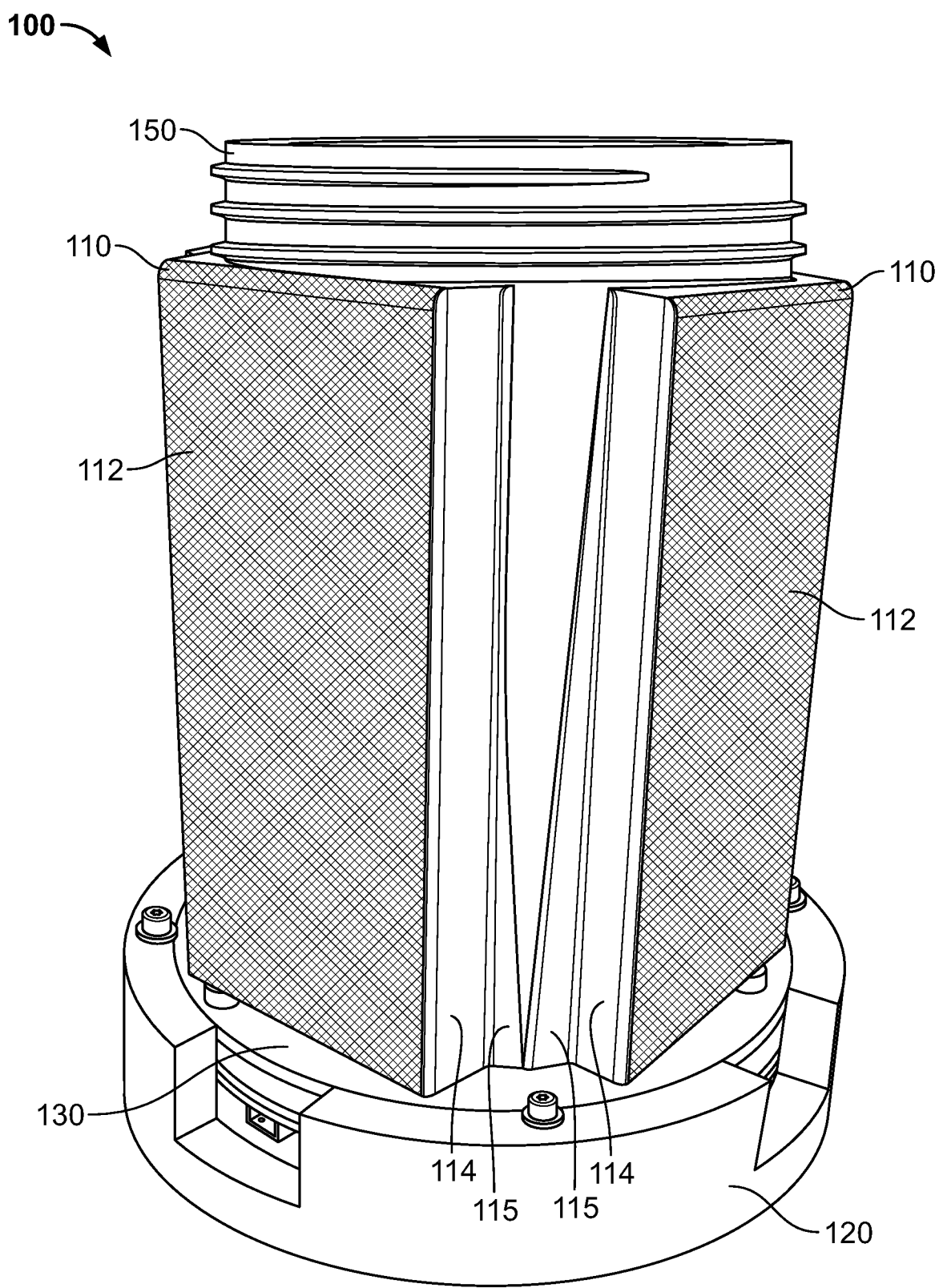
FIG. 1 is a side view illustration of one embodiment of the receptacle of the present specification, depicting the electrolyte container therein.

The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present specification is directed toward methods and systems of monitoring the level and composition of electrolytes in fluid used in dialysis treatment procedures. In one embodiment, the system utilizes active capacitance to determine electrolyte level and composition. Included in the system is a receptacle attached to or positioned proximate a dialysis machine and adapted to receive a container that is used to house electrolytes in a fluid. In one embodiment, the receptacle includes a base and at least two side panels configured to contact the external surface of the container when the container is placed within the receptacle. In one embodiment, the receptacle includes four side panels. In various embodiments, the receptacle includes less than or more than four side panels, provided there are preferably an even number of panels. The panels are made of any insulating material that is rigid enough to support the container. In one embodiment, the panels are composed of plastic.

In one embodiment, the panels are arranged in a circular pattern and their inside surfaces are shaped to match the curvature of the container, thereby insuring a tight fit and maximizing contact between the inner surface of each panel and external surface of the container. In one embodiment, the curvature of the inside surface of each panel is between 2 and 5 degrees concave, or curving inward to each panel and away from the center of the container. The outside surface of each panel can take any shape and, in one embodiment, is flat to ease handling. The inside surface of each panel is covered with a conductive material for use in the capacitance measurements. The conductive material extends beyond the lower edge of the panel and is in electrical contact with a circuit board housed in the base of the receptacle. In one embodiment, the conductive material is copper. The outer surface of each panel is covered in a material for shielding. In one embodiment, the shielding material is copper. The panels are electrically isolated from one another but are in physical contact to insure a tight fitting with the container. In various embodiments, the panels are attached at their sides, tops, and/or bottoms. The receptacle also includes a base, to which each individual panel is attached and on top of which rests the container. In one embodiment, the panels are screwed into the base.

It should be appreciated that, while a circular pattern has been disclosed, the panels may be positioned in rectangular, square, triangular or other polygonal shaped pattern, provided their inside surfaces are shaped to match the external surface of the container, thereby insuring a tight fit and maximizing contact between the inner surface of each panel and external surface of the container, provided the inner surface of each panel is covered with a conductive material, and provided each panel is electrically isolated from one another.

The receptacle includes a circuit board for driving the capacitive process. The circuit board drives capacitance operations to generate and interpret data concerning the level and composition of the electrolytes in the container. In one embodiment, the circuit board is housed in the base. In another embodiment, the circuit board is isolated into a small housing and placed on an external surface of the reservoir and electrically coupled to the receptacle via a wired or wireless contact. In another embodiment, the circuit board is isolated from the receptacle, placed within the dialysis machine, and electrically coupled to the receptacle via a wired or wireless contact. In the embodiments where the circuit board is separate from the receptacle, the receptacle base is a simple physical platform and is detachable from the panels to permit cleaning.

The container can be of any clarity or opacity, and need not be transparent. The outside curvature of the container is shaped to match the curvature of the inside surface of the panels. The height of the container is designed to extend just above the top of the panels. In various embodiments, the container is composed of any non-metallic material, such as glass or plastic.

The receptacle acts as a capacitor and is used to measure the level and composition of a fluid within the container. The capacitance of a pair of parallel plates varies with the spacing and with the dielectric constant of the material which separates the plates of the capacitor. The dielectric is positioned between the two conducting plates, each having an area A and a separation between the plates of d.

The simplest capacitor consists of two parallel conductive plates separated by a dielectric with permittivity $\varepsilon$ (such as air). The plates are considered to extend uniformly over an area A and a charge density $\pm\rho=\pm Q/A$ exists on their surface. Assuming that the width of each plate is much greater than their separation d, the electric field near the center of the device will be uniform with the magnitude $E=\rho/\varepsilon$. The voltage is defined as the line integral of the electric field between the plates:

$$V = \int_0^d E dz = \int_0^d \frac{\rho}{\varepsilon} dz = \frac{\rho d}{\varepsilon} = \frac{Qd}{\varepsilon A}.$$

Solving this for C=Q/V reveals that capacitance increases with area and decreases with separation:

$$C = \frac{\varepsilon A}{d}.$$

Referring to the receptacle of the present specification, the panel area and spacing are fixed. The dielectric constant of the water with electrolytes in solution is much greater than that of air. In one embodiment, the circuit board includes a resistor-capacitor (RC) oscillator. By placing the container with electrolytes in the circuit of an RC oscillator, the frequency of the oscillator becomes a function of the fluid level in the container. The relationship between oscillator frequency and the partial volume of electrolyte as a percentage of the total volume is slightly non-linear. The curve fit to correct for the non-linearity is a simple second order polynomial.

The plates of the capacitor are formed by the electrodes surrounding the container. In one embodiment, grounded shield electrodes are included to minimize the effects of other objects in the vicinity outside of the container. When the container is empty, the frequency of the oscillator is at a maximum. This frequency is in effect set by the combination of a 5 picofarad (pF) capacitor and the stray capacitance in response to the physical layout.

In one embodiment, a second oscillator with a 5 pF capacitor is included but has no connection to the container. This oscillator is used to track the effects of temperature on the fluid within the container.

In one embodiment, the receptacle includes an I2C peripheral comprising an impedance bridge. The impedance bridge measures the dissipation factor of the contents of the container to enable the receptacle to distinguish between water and water with electrolytes dissolved in it.

In one embodiment, the receptacle includes a small serial flash memory for storage of the last calibration values. This will enable the receptacle to have more accurate results after a mid-procedure restart.

During operation, a programmable processor on the circuit board generates alternating current (AC) excitation in the form of a stimulation waveform and transmits it to the conductive material covered inside surface of at least one of the side panels. The circuit board then receives, and measures, a responsive waveform indicative of the electrically coupled response from the conductive material covered inside surface of the opposing side panel. The measured capacitance will change depending on the volume and composition of the electrolytes in the container. Measured values are then compared with previously calculated capacitance values of known liquids and volumes to determine the electrolyte level and composition.

In one embodiment, the system is calibrated before providing a container with an electrolyte solution. During calibration, the receptacle measures the capacitance of an empty and present container. The empty container capacitance is set at zero, effectively taring the system. The system is further calibrated by providing an AC excitation and measuring the coupled response for a set of liquids whose volume and electrolyte level are known. Preferably, the calibration is a one-time manufacturing process and performed in a closed environment using a crystal oscillator to measure capacitance.

In one embodiment, the processor is programmed to provide AC excitation and record capacitance measurements, in a local memory, at predetermined intervals. In one embodiment, the predetermined interval is every one second. In one embodiment, the system operates at 3.3 V and is configured to differentiate between pure water and electrolyte solutions containing differing concentrations of potassium, magnesium, and/or calcium.

The present specification is also directed toward a method and system of monitoring the level and composition of electrolyte used in dialysis treatment procedures through the use of induction measurements. In one embodiment, the system comprises a base and a receptacle having a pair of intertwined, mutually shielded conductive coils that wrap around a container with electrolyte. Mutual inductance is measured between the two coils on opposing sides of the container to determine liquid level. Temperature measurements can be combined with the inductance measurement to determine liquid composition. In one embodiment, the device is factory calibrated using known liquids and levels.

In another embodiment, the system utilizing inductance comprises a base and a receptacle having a single conductive coil that wraps around a container with electrolyte. Single inductance is measured between the coil on side of the container and the coil on the opposite side of the container to determine liquid level. Temperature measurements can be combined with the inductance measurement to determine liquid composition. In one embodiment, the device is factory calibrated using known liquids and levels.

The present specification is also directed toward a method and system of monitoring the level and composition of electrolyte used in dialysis treatment procedures through the use of ultrasonic measurements. The ultrasonic measurements are taken and interpreted using methods and systems similar to those described in U.S. Pat. No. 7,661,294, entitled "Non-invasive multi-function sensor system" and assigned to the applicant of the present invention and to Measurement Specialties, Inc., which is herein incorporated by reference in its entirety.

Referring to FIG. 1, a side view illustration of one embodiment of the receptacle 100, depicting the electrolyte container 150, is shown. The receptacle 100 comprises a plurality of side panels 110 which, when assembled with the receptacle base 120, form a cavity for receiving the container 150. The side panels 110 preferably have an internal surface that is curved to match the curvature of the container 150. The entire panel 110, however, need not be curved with the outside being able to have a variety of different curved, straight, or angular surfaces.

Figure 2:
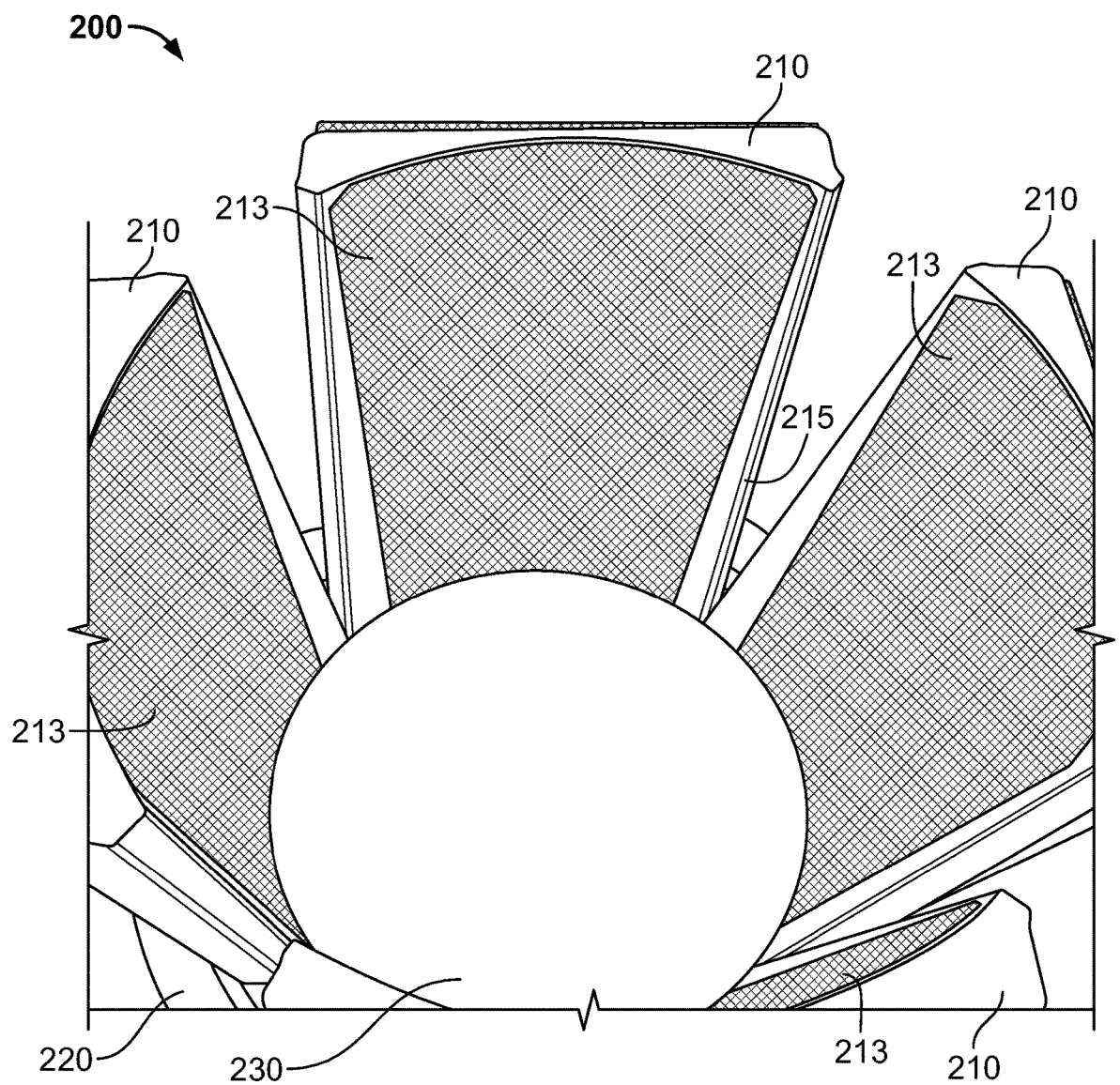
FIG. 2 is an oblique top view illustration of one embodiment of the inside of the receptacle of the present specification.

The outer surface of each panel 110 is covered by a shielding material 112. The inside surface of each panel 110 is covered by a metallic material (as seen in FIG. 2) for use in the capacitive process. Each panel 110 is electrically isolated from the other panels 110. Neither the shielding material 112 nor the metallic material extends onto the side surfaces 114 of adjacent panels 110. In one embodiment, extending from both side surfaces 114 of each panel is a fin 115. Two opposing fins 115 come into physical contact at the base 120 of the receptacle. The fins 115 recede toward the side surface 114 as they extend up along the side of each panel such that they are flush with the side surface 114 once they reach the top edge of the panel 110. The fins 115 are not covered by any conductive elements so that the panels remain electrically isolated. The physical alignment of the fins 115 at the base 120 act to create a more secure fit for the container 150.

In the pictured embodiment, the electronics 130 of the receptacle 100 are housed in the base 120. In one embodiment, the conductive material on the inside surface of each panel 110 extends beyond the bottom edge of the panel and is electrically connected to the electronics 130 in the base 120. This allows for the generation of a stimulation waveform from the electronics 130 and through the conductive material for the capacitance measurement. In another embodiment, the electronics are not housed in the base and conductive wires extend from the bottom of each panel 110 through a distance, which may include into the dialysis machine itself, to electrically connect the conductive material with the electronics.

The panels may be fixedly or removably attachable to the base. For example, the panels may be permanently welded, molded, or glued into or onto the top surface of the base. The panels may also be removably attached into or onto the top surface of the base by having the panels positioned in slots in the base surface, attached by latches, hooks, or other attachment means.

FIG. 2 is an oblique top view illustration of one embodiment of the inside of the receptacle 200. The electrolyte container has been removed to assist in visualization. The inside surface of each panel 210 is covered with a metallic material 213 for use in the inductive process. The bottom portions of opposing fins 215 meet at the base 220 to increase stability. Once again, in the pictured embodiment, the electronics 230 of the receptacle 200 are housed in the base 220.

Figure 3:
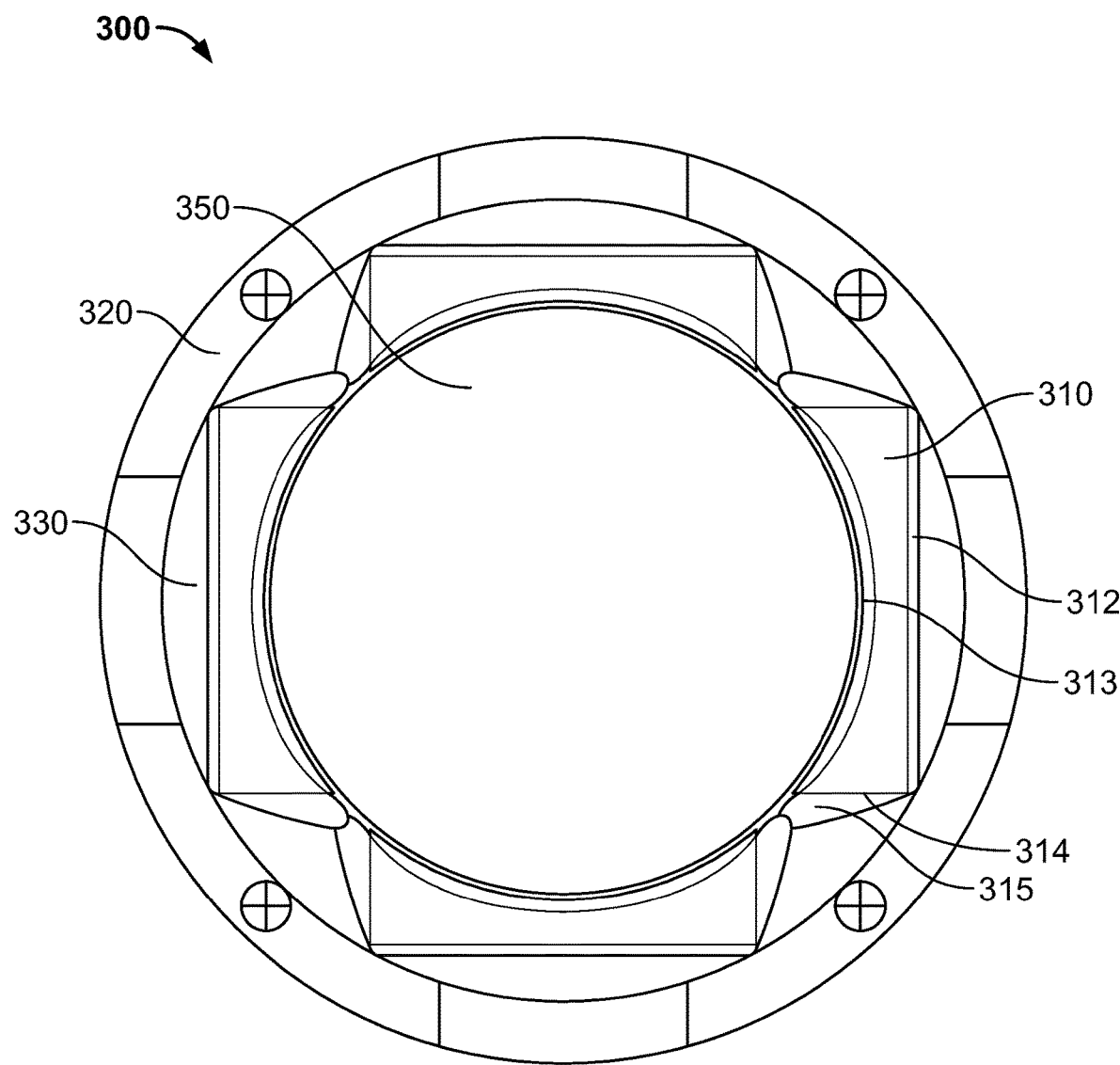
FIG. 3 is a top down view illustration of one embodiment of the receptacle of the present specification, depicting the electrolyte container therein.

FIG. 3 is a top down view illustration of one embodiment of the receptacle 300, depicting the electrolyte container 350 therein. In the pictured embodiment, the receptacle 300 comprises four panels 310 and a base 320. Each panel 310 includes a shielding cover 312 on its outer surface, a metallic material 313 on its inner surface, a side surface 314 on each lateral side of each panel 310 and a tapering fin 315, which tapers toward the top and is thickest at the bottom, extending from each lateral side surface 314. The shielding cover 312 and metallic material 313 do not extend over the side surfaces 314 or fins 315, thereby keeping the panels 310 electrically isolated from one another. The base 320 includes the electronics 330 that generate the stimulation wave, receive the responsive wave, store calibration data, and calculate fluid levels and electrolyte compositions based on the responsive wave and stored calibration data.

Figure 4:
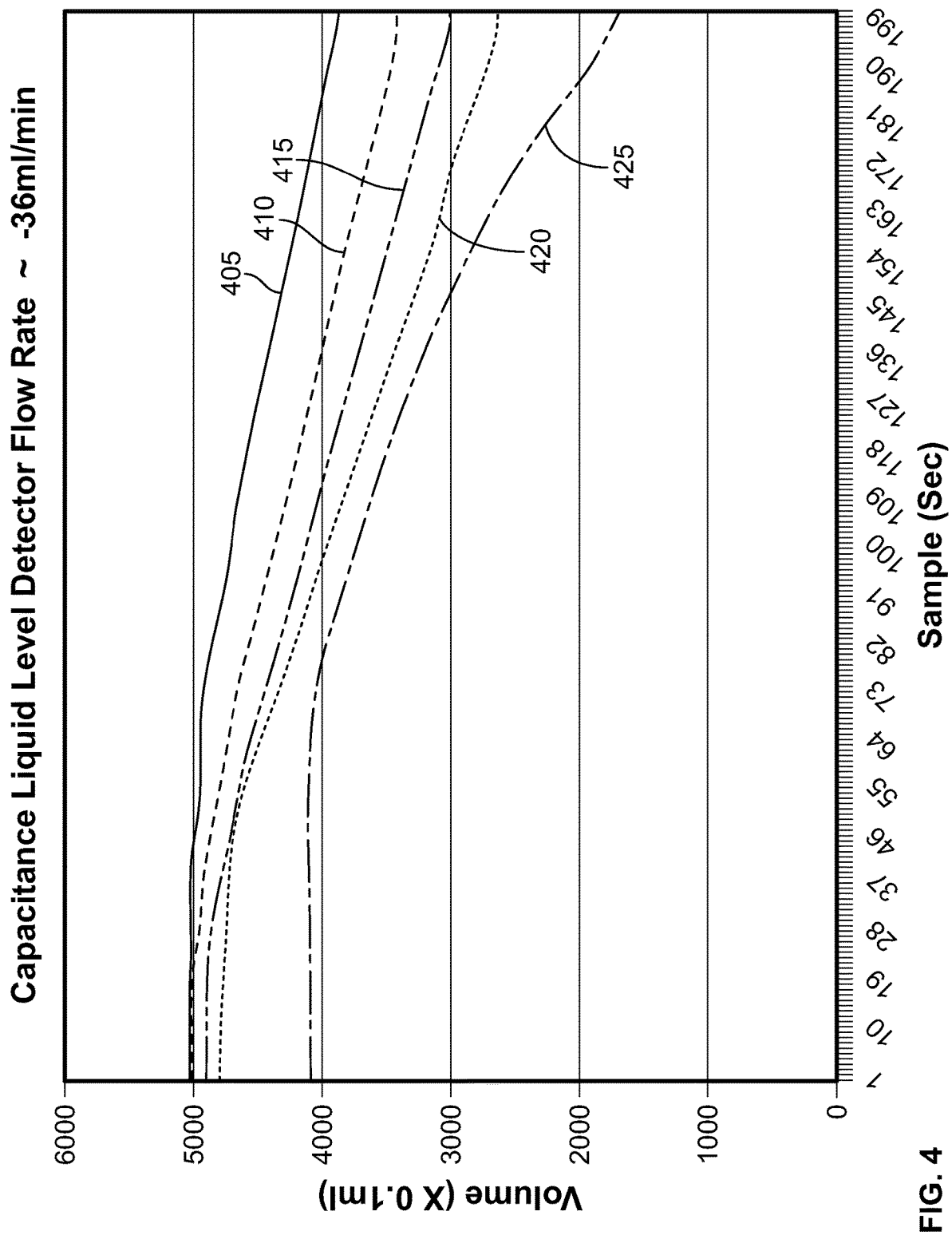
FIG. 4 is an exemplary line graph depicting the volume of a number of electrolytes within a solution over time as measured using a capacitance method in accordance with one embodiment of the present specification; and, FIG. 5 is an exemplary line graph depicting the volume of a number of electrolytes within a solution over time as measured using an ultrasonic method in accordance with one embodiment of the present specification.

FIG. 4 is an exemplary line graph depicting the volume of water and a number of electrolytes within a solution over time as measured using a capacitance method in accordance with one embodiment of the present specification. The graph illustrates the levels of water 405, K2 410, K3 415, NaCl(60) 420, and KCl+(1 mol) 425 over time at a dialysis flow rate of approximately 36 ml/min. The volumes of water and the electrolytes can be seen decreasing over time as the solution is used by the dialysis system. Such a graph can be compared to known values of water and electrolytes processed at the same rate to determine current solution level and composition.

Figure 5:
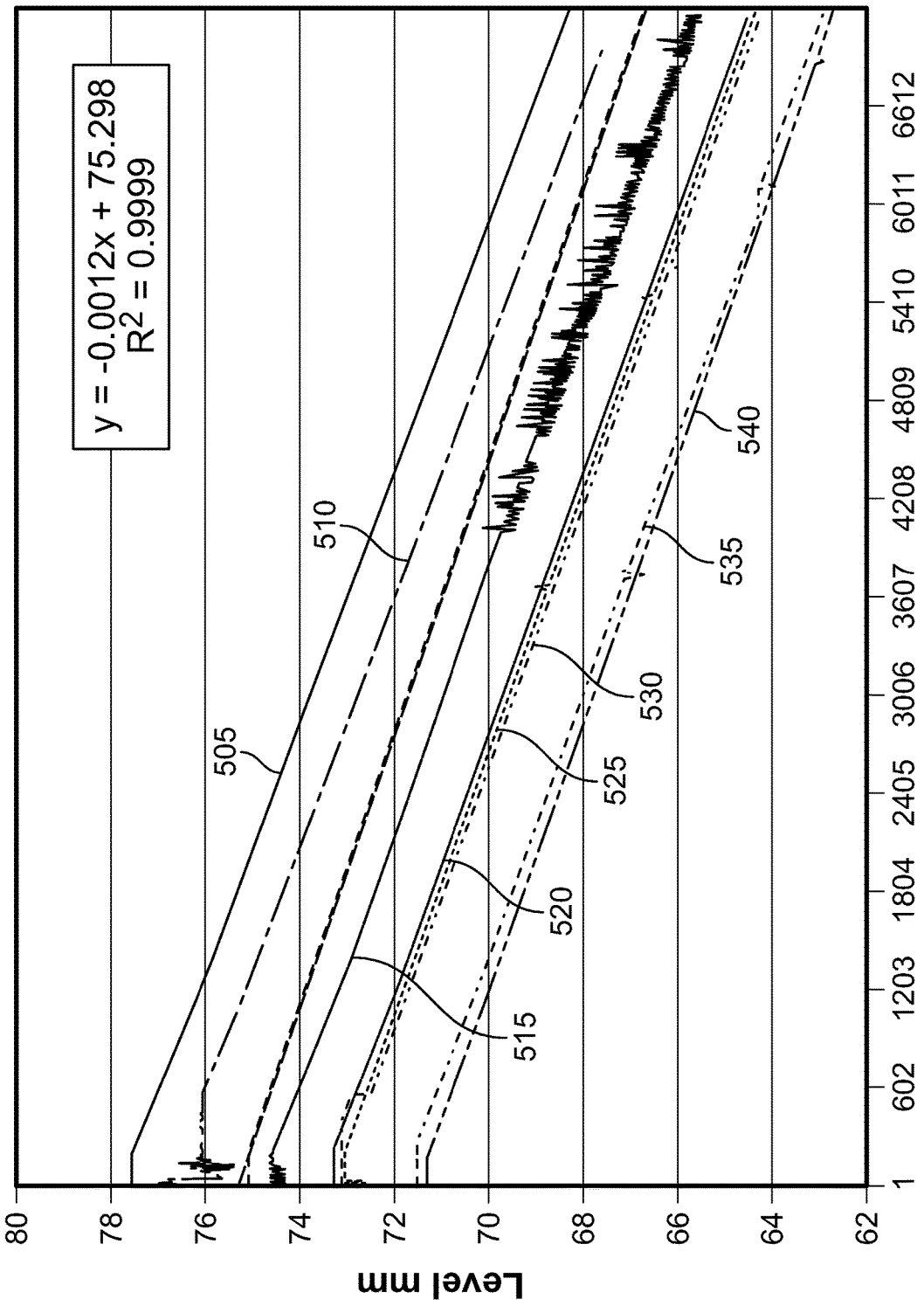

FIG. 5 is an exemplary line graph depicting the volume of water and a number of electrolytes within a solution over time as measured using an ultrasonic method in accordance with one embodiment of the present specification. The graph illustrates the levels of water 505, $Na_2CO_3$ 510, Low K 515, K1+Ca 0.5 520, K1 525, K1+(1 mol) 530, K2 535, and K3 540 over time at a dialysis flow rate of approximately 1 ml/min for 1 hour. The graph also includes a linear measure line 550 for reference. The volumes of water and the electrolytes can be seen decreasing over time as the solution is used by the dialysis system. Such a graph can be compared to known values of water and electrolytes processed at the same rate to determine current solution level and composition. When compared to the graph of FIG. 4, the values decrease in a more linear fashion.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A method of monitoring a fluid having a fluid level and electrolytes in a dialysis system, the method comprising the steps of:
providing a receptacle configured to receive a container, wherein the receptacle comprises a base, a first panel attached to the base, a second panel attached to the base, and circuitry in electrical communication with the first panel and the second panel, wherein each of the first and second panels comprises an inner surface facing the container, wherein each of the first and second panels includes a conductive material on its inner surface, and wherein each panel is electrically isolated from each other panel;
filling the container with the fluid and the electrolytes;
operatively connecting a fluid flow path from a dialysate circuit in the dialysis system to the container;
performing a dialysis treatment on a patient using the dialysate circuit;
operating the circuitry to generate an electrical excitation of the conductive material on the inner surface of the first panel;
measuring a capacitance, arising from the electrical excitation of the conductive material on the inner surface of the first panel, in the second panel; and
determining the fluid level and a composition of the electrolytes based on the measured capacitance.

2. The method of monitoring a fluid of claim 1 wherein the electrolytes are at least one of potassium, magnesium, and calcium.

3. The method of monitoring a fluid of claim 1 wherein the circuitry comprises a processor and memory storing programmatic instructions that, when executed, generates an alternating current in a form of a stimulation wave and transmits such wave to the first panel.

4. The method of monitoring a fluid of claim 3 wherein the circuitry comprises a processor and memory storing programmatic instructions that, when executed, receives and processes a responsive signal generated by the second panel in response to an electrical stimulation of the first panel.

5. The method of monitoring a fluid of claim 4 wherein the circuitry comprises a processor and memory storing programmatic instructions that, when executed, compares data derived from the responsive signal to predetermined capacitance data for liquids with known levels and known electrolyte compositions.

6. The method of monitoring a fluid of claim 5 wherein the circuitry comprises a processor and memory storing programmatic instructions that, when executed, determines the fluid level and the composition of the electrolytes in the fluid based on the data derived from the responsive signal and the predetermined capacitance data.

7. The method of monitoring a fluid of claim 6 wherein the circuitry comprises a processor and memory storing programmatic instructions that, when executed, receives data indicative of a temperature from a temperature sensor, applies a function of the data indicative of a temperature and data derived from the responsive signal to generate an output, compares the output to data derived from compositions of liquids having known levels of electrolytes and temperatures, and, based on the comparison, determines the composition of the electrolytes in the fluid.

8. The method of monitoring a fluid of claim 1 wherein the circuitry comprises a processor and memory storing programmatic instructions that, when executed, causes the circuitry to generate electrical excitation and record capacitance measurements, in a local memory, at predetermined intervals.

9. The method of monitoring a fluid of claim 1 wherein the circuitry comprises a resistor-capacitor (RC) oscillator and wherein a frequency of the oscillator defines a function of the fluid level in the container.

10. The method of monitoring a fluid of claim 9 wherein the circuitry comprises a second oscillator adapted to track one or more effects of temperature on the fluid within the container.

11. The method of monitoring a fluid of claim 1 wherein the receptacle comprises an impedance bridge adapted to measure a dissipation factor of contents of the container to distinguish between fluid and fluid with electrolytes dissolved in it.

12. The method of monitoring a fluid of claim 1 wherein the receptacle comprises serial flash memory for storage of calibration values.

13. The method of monitoring a fluid of claim 1 wherein the receptacle comprises grounded shielded electrodes to minimize one or more effects of objects in a vicinity outside the container.

14. The method of monitoring a fluid of claim 1 wherein the circuitry is housed within the base of the receptacle.

15. The method of monitoring a fluid of claim 1 wherein the circuitry is housed in a compartment located external to the receptacle.

16. The method of monitoring a fluid of claim 1 wherein the conductive material is copper.

17. The method of monitoring a fluid of claim 1 wherein each of the first and second panels comprises an outer surface opposite the inner surface, wherein each outer surface comprises a shielding material, and wherein the shielding material is copper.

18. The method of monitoring a fluid of claim 1 wherein the receptacle in combination with each of the first and second panels forms a structure defining a cavity that is substantially cylindrical.

19. The method of monitoring a fluid of claim 1 wherein the container is configured to snugly fit within the receptacle, maximizing contact between the inner surface of each of the first and second panels and an external surface of the container.

20. The method of monitoring a fluid of claim 1, further comprising calibrating a system comprising the receptacle and container by:
 measuring a capacitance of an empty container received in the receptacle; and
 measuring a capacitance of at least one liquid having a known volume and known electrolyte levels.

21. The method of monitoring a fluid of claim 1 wherein the inner surface is curved.

* * * * *